United States Patent [19]

Hughes

[11] Patent Number: 4,730,500
[45] Date of Patent: Mar. 15, 1988

[54] VORTEX GENERATING MASS FLOWMETER

[75] Inventor: Nathaniel Hughes, Palm Springs, Calif.

[73] Assignee: Vortran Corporation, Culver City, Calif.

[21] Appl. No.: 570,162

[22] Filed: Jan. 12, 1984

Related U.S. Application Data

[63] Continuation-in-part of Ser. No. 213,843, Dec. 8, 1980, Pat. No. 4,453,542, which is a continuation-in-part of Ser. No. 40,557, May 21, 1979, Pat. No. 4,240,293, and Ser. No. 109,839, Jan. 7, 1980, Pat. No. 4,372,169.

[51] Int. Cl.$^4$ ............................ G01F 1/32; G01F 1/44
[52] U.S. Cl. ............................ 73/861.22; 73/861.52; 73/861.42
[58] Field of Search ............ 73/861.22, 861.24, 861.61, 73/861.52, 861.65, 861.03, 861.66, 861.42

[56] References Cited

U.S. PATENT DOCUMENTS

| | | | |
|---|---|---|---|
| 1,145,234 | 7/1915 | Dodge | 73/861.66 |
| 1,935,445 | 11/1933 | Heinz | 73/861.24 |
| 3,116,639 | 1/1964 | Bird | 73/861.24 |
| 3,719,073 | 3/1973 | Mahon | 73/861.22 |
| 3,785,204 | 1/1974 | Lisi | 73/861.03 |
| 3,940,986 | 3/1976 | Yamasaki et al. | 73/861.23 |
| 4,161,878 | 7/1979 | Fussell, Jr. | 73/861.24 |
| 4,285,246 | 8/1981 | Kitu | 73/861.03 |
| 4,404,858 | 9/1983 | Belchinger | 73/861.22 |
| 4,481,828 | 11/1984 | Cheng | 73/861.66 |
| 4,523,477 | 6/1985 | Miller | 73/861.22 |

*Primary Examiner*—Herbert Goldstein
*Attorney, Agent, or Firm*—Christie, Parker & Hale

[57] ABSTRACT

One or more rods are employed in the flow passage of the above-described flowmeter as the drag-producing bluff body. Conveniently, the rods can also serve as probes for sensing the pressure in the flow passage. In the preferred embodiment, one rod is radially oriented upstream of the restriction and another rod is radially oriented at an angle to the first rod within the restriction. The rods have hollow interiors connected to a ΔP transducer. The first rod has a chamfered end facing upstream.

27 Claims, 10 Drawing Figures

VORTEX GENERATING MASS FLOWMETER

CROSS REFERENCE TO RLEATED APPLICATIONS

This is a continuation-in-part of application Ser. No. 213,843, filed Dec. 8, 1980, now U.S. Pat. No. 4,453,542 which is a continuation-in-part of application Ser. No. 40,557, filed May 21, 1979, now U.S. Pat. No. 4,240,293, and Ser. No. 109,839, filed Jan. 7, 1980, now U.S. Pat. No. 4,372,169. The disclosures of these applications are incorporated fully herein by reference.

BACKGROUND OF THE INVENTION

This invention relates to gas flow rate measurement and, more particularly, to a vortex generating mass flowmeter usable over a wide range of flow rates.

There are many different types of flowmeters in use today. One type, which is known as a vortex shedding flowmeter, generates intermittent, unstable vortices with a transversely elongated bluff body positioned in the flow stream passing through an unrestricted fluid line. The frequency of the intermittent vortices or perturbations is a measure of the flow rate through the fluid line, and this frequency is sensed to provide a flow rate reading. The devices are generally limited to liquid flow rate measurement due to the effect of compressibility the gas on the vortex shedding process. A typical vortex shedding flowmeter is disclosed on Rodely U.S. Pat. No. 3,572,117, issued Mar. 23, 1971.

Another type of flowmeter measures the pressure difference across a calibrated orifice plate. In the case of gas measurement, due to compressibility effects, the mass flow rate is not only dependent upon the pressure difference but also temperature and density variations, and the relationship is nonlinear and highly complex. Thus, the measured pressure difference must be processed further to give a true reading of mass flow rate. These devices generally read gas flow over a limited range due to rapidly increasing pressure difference across the device.

My U.S. Pat. Nos. 4,240,293 and 4,372,169 disclose a flowmeter that utilizes the aerodynamic drag resulting from a bluff body to generate a pressure signal related to flow rate. The flowmeter comprises a flow passage in which a restriction is formed, a bluff body, in the form of one or more discs or truncated cones disposed on one side of the restriction, and a pressure sensor.

SUMMARY OF THE INVENTION

According to the invention, one or more rods are employed in the flow passage of the above-described flowmeter as the drag-producing bluff body. Conveniently, the rods can also serve as probes for sensing the pressure in the flow passage. In the preferred embodiment, one rod is radially oriented upstream of the restriction and another rod is radially oriented at an angle to the first rod within the restriction. The rods have hollow interiors connected to a ΔP transducer. The first rod has a chamfered end facing upstream.

BRIEF DESCRIPTION OF THE DRAWINGS

The features of specific embodiments of the best mode contemplated of carrying out the invention are illustrated in the drawings, in which.

DETAILED DESCRIPTION OF THE SPECIFIC EMBODIMENTS

The disclosures of my U.S. Pat. Nos. 4,240,293 and 4,372,169 are incorporated fully herein by reference. These patents describe a number of flowmeters employing frustums as vortex-generating bluff bodies. It has now been discovered that rods extending into the flow passage transverse to the direction of flow can also serve advantageously as vortex-generating bodies in a flowmeter employing the principles of the above-mentioned patents.

Figure 1:
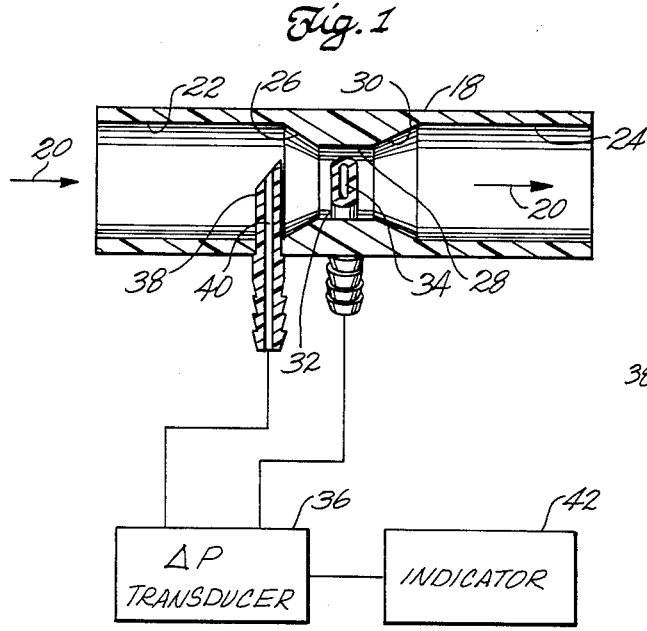
FIGS. 1 and 2 are side-sectional and upstream end-sectional views, respectively, of a flowmeter incorporating principles of the invention.
Figure 2:
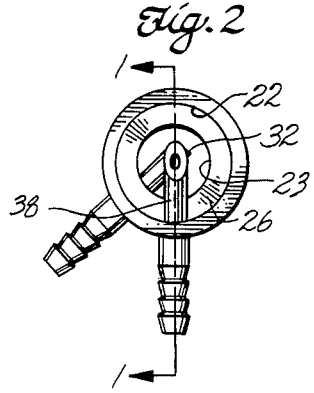

In FIGS. 1 and 2, fluid, preferably gas, flows through a pipe 18 in the direction of arrows 20. Pipe 18 has a cylindrical upstream chamber 22 and a cylindrical downstream chamber 24 that are connected by a converging section 26, a cylindrical section 28, and a diverging section 30, all smaller in diameter than chambers 22 and 24. The divergence of section 28 is more gradual than the convergence of section 26. Chamber 22 serves as an inlet port and chamber 24 serves as an outlet port. Sections 26, 28, and 30 serve as a restriction in the flow passage. A rod 32 extends radially into cylindrical section 28 beyond the center of the passage. Means for sensing gas pressure in the form of passage 34 through rod 32 is connected to one inlet of a ΔP transducer 36. In the embodiment of FIG. 1, the end of rod 32 in the flow passage is squared off. A rod 38 for producing drag extends radially through chamber 22 at its junction with section 26, to form an acute angle with rod 32 as depicted in FIG. 2. A passage 40 through rod 38 is connected to another inlet of ΔP transducer 36. Rod 38 extends to the center of the flow passage. The end of rod 38 is chamfered to face in an upstream direction. ΔP transducer 36 is connected to an indicator 42 that displays in analog or digital form the pressure difference between the end of rod 34 and the end of rod 38.

Considering the small diameter of rods 32 and 38, a large pressure differential signal is generated, which is indicateve of large drag. Typical dimensions for the described flowmeter are as follows:

| | |
|---|---|
| Diameter of chambers 22 and 24 | .612 inch |
| Diameter of rod 32 | .075 inch |
| Diameter of rod 38 | .075 inch |
| Length of rod 32 | .950 inch |
| Length of rod 38 | .950 inch |
| Chamfer on rod 38 | 45 degrees |
| Base diameter of section 26 | .520 inch |
| Included angle of section 26 | 45 degrees |

-continued

| | |
|---|---|
| Base diameter of section 30 | .520 inch |
| Included angle of section 30 | 21 degrees |
| Diameter of section 28 | .342 inch |
| Length of section 28 | .310 inch |
| Spacing between rods 32 and 38 | .400 inch |
| Angle between rods 32 and 38 | 45 degrees |

Figure 3:
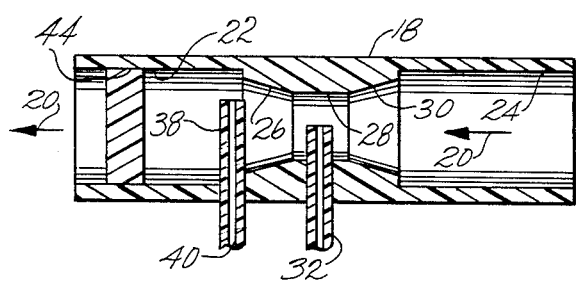
FIGS. 3 and 4 are side-sectional and upstream end-sectional views of another embodiment of a flowmeter incorporating principles of the invention.
Figure 4:
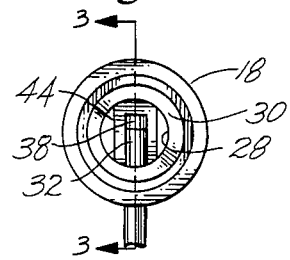
Figure 5:
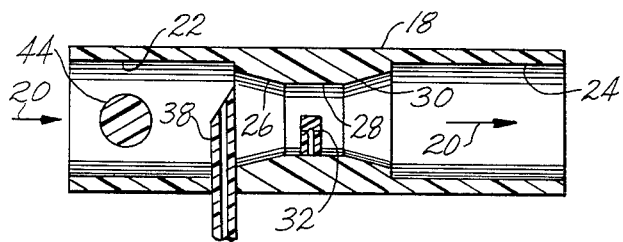
FIGS. 5 and 6 are side-sectional and downstream end-sectional views, respectively, of still another embodiment of a flowmeter incorporating principles of the invention.
Figure 6:
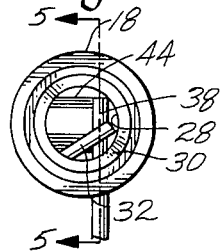
Figure 7:
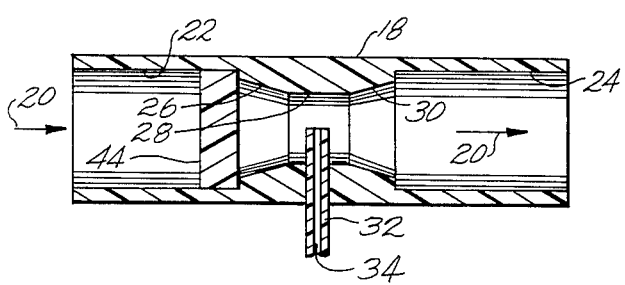
FIGS. 7 and 8 are side-sectional and downstream end-sectional views, respectively, of still another embodiment of a flowmeter incorporating principles of the invention.
Figure 8:
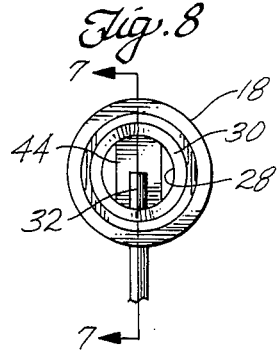

In the embodiments of FIGS. 3 through 10, the same reference numerals are used to identify the components in common with the embodiment of FIGS. 1 and 2. In the embodiment of FIGS. 3 and 4, rod 32 extends to the center of the flow passage, rod 38 extends beyond the center of the flow passage and has a squared off end. A thick, cylindrical rod 44 extends diametrically across the flow passage upstream of rod 38. In the embodiment of FIGS. 5 and 6, rods 32 and 38 are both oriented on different chords. The end of rod 32 is squared off and the end of rod 38 is chamfered to face in an upstream direction. In the embodiment of FIGS. 7 and 8, rod 38 is eliminated and passage 34 is connected to a single inlet pressure sensor to provide an absolute pressure reading. Also, rod 44 for producing drag is located at the junction of chamber 22 and section 26.

Figure 9:
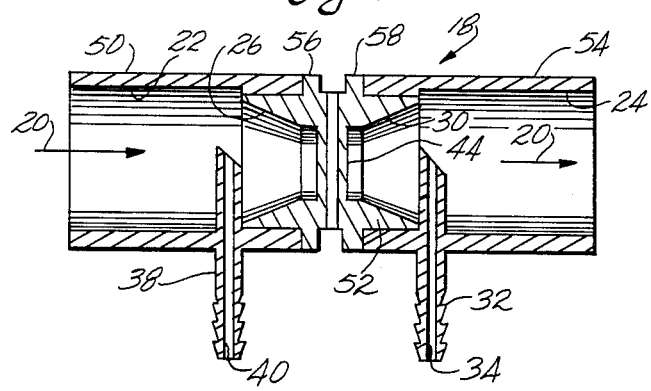
FIGS. 9 and 10 are side-sectional and downstream end-sectional views, respectively, of yet another embodiment of a flowmeter incorporating principles of the invention.
Figure 10:
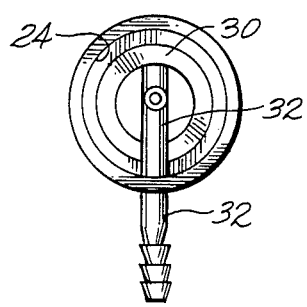

In the embodiment of FIGS. 9 and 10, first and second rods 32 and 38 are both chamfered to face in the same direction. Rod 32 extends radially through chamber 24 at its junction with section 30 to a point beyond the center of the flow passage. Rod 38 extends radially through chamber 22 at its junction with section 26 to a point beyond the center of the flow passage. Passages 34 and 40 are connected to the respective inlets of a ΔP transducer not shown, which is in turn connected to an indicator. The axes of rods 32 and 38 are aligned. A cylindrical rod 44 extends diametrically across section 28. Its axis is aligned with the axes of rods 32 and 38. The divergence of section 30 is the same as the convergence of section 26, both of which are more gradual than the corresponding sections in the other embodiments. The vortex activity created by rod 44 in this embodiment produces a different signal than the other embodiments because what is being measured is vortex activity within vortex activity. In effect, there is a flowmeter within a flowmeter and the square law governing the signal generated by rods 32 and 38 is offset by the square root relationship of the orifice presented by section 23 and rod 44. The result is a more linear signal as a function of flow rate. Further, this design provides symmetrical, bidirectional flow response—the response is positive at passage 40 with respect to passage 34 for flow in the direction of arrow 20 and positive at passage 34 with respect to passage 40 for flow in the other direction, while the magnitude in both cases is the same for a given flow rate. The flowmeter can be calibrated for different flow rates by changing the diameter of rod 44 or providing as a substitute therefor drag bodies having different shapes, such as a sphere or an aerodynamic foil. Further, this flowmeter appears to have a broader range of operation than the other embodiments. Of importance is the fact that this embodiment can be used to measure either liquid or gas flow with comparable results. The difference in density between liquids and gases can be compensated for by increasing the diameter of rod 44 However, in many cases the same design can be used to measure both liquids and gases. In practice the diameters of rods 32, 38, and 44 can be scaled up or down without any ill effects. The sizes of these rods determines the signal-to-ΔP ratio of the flowmeter.

In practice, the embodiment of FIGS. 9 and 10 is preferably fabricated from three injection-molded plastic parts designated 50, 52, and 54. Chamber 22 and rod 38 are formed in part 50. Chamber 24 and rod 32 are formed in part 54. Sections 26, 28, and 30 and rod 44 are formed in part 52. Parts 50 and 54 are standard interchangeably fit together with several different versions of part 52 having a rod 44 with different diameters. As illustrated in FIG. 9, part 52 has annular external shoulders 56 and 58 against which the ends of parts 50 and 54, respectively, abut. Typical dimensions for the described flowmeter are as follows:

| | |
|---|---|
| Diameter of chambers 22 and 24 | .620 inch |
| Diameter of rods 32 and 38 | .104 inch |
| Length of rods 32 and 38 | .950 inch |
| Chamfer on rod 38 | .335 degrees |
| Base diameter of sections 26 and 30 | .520 inch |
| Included angle of sections 26 and 30 | 21 degrees |
| Diameter of section 28 | .342 inch |
| Length of section 28 | .310 inch |
| Center-to-center spacing between | |
| rods 32 and 44 | .451 inch |
| and 38 and 44 | _ inch |

The described embodiments of the invention are only considered to be preferred and illustrative of the inventive concept; the scope of the invention is not to be restricted to such embodiments. Various and numerous other arrangements may be devised by one skilled in the art without departing from the spirit and scope of this invention. For example, some of the embodiments operate with a flow direction opposite to that illustrated. Further, the sensitivity of a number of the embodiments disclosed herein, particularly FIG. 9, can be increased by employing a bypass arrangement as disclosed in FIG. 2 or FIG. 5 of the above-referenced U.S. Pat. No. 4,372,169.

What is claimed is:

1. A vortex generating flowmeter comprising:
   a first port;
   a second port;
   a flow measurement passage between the ports;
   a restriction formed in the flow passage between the first and second ports, the restriction comprising a converging-diverging nozzle;
   a rod producing drag in the passage between the restriction and the second port; and
   means for sensing gas pressure in the vicinity of the rod.

2. The flowmeter of claim 1, in which the first port, the second port, and the passage are aligned with a common flow axis.

3. The flowmeter of claim 2, in which the rod lies in a plane transverse to the flow axis.

4. The flowmeter of claim 3, in which the converging-diverging nozzle has a cylindrical throat section between the converging and diverging sections of the nozzle.

5. The flowmeter of claim 4, in which the portion of the passage between the restriction and the second port is cylindrical and larger in cross-sectional area than the nozzle.

6. The flowmeter of claim 5, in which the sensing means comprises a pressure sensor and a passage through the rod from the interior of the flow measurement passage to the pressure sensor.

7. The flowmeter of claim 6, additionally comprising a rod extending into the restriction in a plane transverse to the flow axis.

8. The flowmeter of claim 7, in which the pressure sensor is a ΔP transducer having first and second inlets, a passage through the first recited rod being connected to the first inlet, the flowmeter additionally comprising a passage through the rod extending into the restriction and being connected to the second inlet.

9. The flowmeter of claim 8, in which the first rod is chamfered to face away from the restriction.

10. The flowmeter of claim 9, in which the rod extending into the restriction is squared off.

11. The flowmeter of claim 10, in which the rod extending into the restriction extends into the restriction beyond the center of the passage.

12. The flowmeter of claim 11, in which the rods are oriented at an angle to each other.

13. The flowmeter of claim 1, additionally comprising a rod extending into the restriction in a plane transverse to the flow axis.

14. The flowmeter of claim 13, additionally comprising a thick rod in the passage between the second port and the first recited rod.

15. The flowmeter of claim 14, in which the thick rod is diametrically disposed all the way across the passage.

16. The flowmeter of claim 15, in which the thick rod is longitudinally aligned with the rod in the restriction.

17. The flowmeter of claim 15, in which the thick rod is transverse to the rod in the restriction.

18. The flowmeter of claim 17, in which one of the first rod and the second recited rod is chordially arranged.

19. The flowmeter of claim 17, in which the first and second rods are chordially arranged.

20. The flowmeter of claim 13, in which the first and the second recited rods form an angle of approximately 30° with each other.

21. The flowmeter of claim 13, in which the sensing means comprises a pressure sensor and further comprises a passage through the rod extending into the restriction from the interior of the flow measurement passage to the pressure sensor.

22. The flowmeter of claim 7, in which the first named rod is on one side of the restriction, the flowmeter additionally comprising a second rod extending into the passage on the other side of the restriction.

23. The flowmeter of claim 22, in which the first and second rods are both chamfered to face in the same direction.

24. The flowmeter of claim 23, in which the rod extending into the restriction extends completely across the passage.

25. The flowmeter of claim 24, in which the first and second rods extend approximately to the middle of the passage.

26. The flowmeter of claim 25, in which the pressure sensor is a ΔP transducer having first and second inlets and the second rod comprises a passage, the passage through the first rod being connected to the first inlet, and the passage through the second rod being connected to the second inlet.

27. The flowmeter of claim 26, in which the rod extending into the restriction is thicker than the first and second rods.

* * * * *